United States Patent
Gross et al.

[11] Patent Number: 5,991,655
[45] Date of Patent: Nov. 23, 1999

[54] IONTOPHORETIC DRUG DELIVERY DEVICE AND METHOD OF MANUFACTURING THE SAME

[75] Inventors: Joseph Gross, Dublin, Ireland; Gilad Lavi, Holon, Israel

[73] Assignee: Drug Delivery Systems, Inc., N.Y.

[21] Appl. No.: 09/031,335

[22] Filed: Feb. 26, 1998

Related U.S. Application Data

[60] Provisional application No. 60/038,131, Mar. 3, 1997.

[51] Int. Cl.[6] ................................................. A61N 1/30
[52] U.S. Cl. ................................. 604/20; 607/152
[58] Field of Search .............................. 604/20; 607/115, 607/145, 152, 153

[56] References Cited

U.S. PATENT DOCUMENTS

| | | | |
|---|---|---|---|
| 4,381,012 | 4/1983 | Russek | 128/644 |
| 4,834,978 | 5/1989 | Nuwayser | 424/448 |
| 4,848,353 | 7/1989 | Engel | 128/640 |
| 4,856,188 | 8/1989 | Sibalis | 604/20 |
| 4,865,582 | 9/1989 | Sibalis | 604/20 |
| 4,931,046 | 6/1990 | Newman | 604/20 |
| 4,950,229 | 8/1990 | Sage, Jr. | 604/20 |
| 5,246,418 | 9/1993 | Haynes et al. | 604/20 |
| 5,314,502 | 5/1994 | McNichols et al. | 604/20 |
| 5,320,597 | 6/1994 | Sage, Jr. et al. | 604/20 |
| 5,337,748 | 8/1994 | McAdams et al. | 128/640 |
| 5,374,242 | 12/1994 | Haak et al. | 604/20 |
| 5,385,543 | 1/1995 | Haak et al. | 604/20 |
| 5,402,780 | 4/1995 | Faasse, Jr. | 607/149 |
| 5,421,816 | 6/1995 | Lipkovker | 604/20 |
| 5,458,569 | 10/1995 | Kirk, III et al. | 604/20 |
| 5,474,527 | 12/1995 | Bettinger | 604/19 |
| 5,498,235 | 3/1996 | Flower | 604/20 |
| 5,551,953 | 9/1996 | Lattin et al. | 604/20 |
| 5,785,040 | 7/1998 | Axelgaard | 128/640 |
| 5,788,666 | 8/1998 | Atanasoska | 604/20 |
| 5,853,383 | 12/1998 | Murdock | 604/20 |
| 5,879,322 | 3/1999 | Lettin et al. | 604/20 |

FOREIGN PATENT DOCUMENTS

WO 91/15257    10/1991    WIPO .

*Primary Examiner*—Wynn Wood Coggins
*Assistant Examiner*—Sharon Finkel
*Attorney, Agent, or Firm*—Factor and Shaftal

[57] ABSTRACT

An iontophoretic drug delivery device comprising a flexible reservoir sandwiched between a flexible printed circuit board and a pair of flexible electrodes. A rigid top cover is mounted on a spine on the reservoir by means of snap-fit connections. The rigid cover protects the device from damage while the flexible reservoir, circuit board and electrodes can conform to the skin of a subject. The configuration of the flexible elements allows the manufacturing process to be simplified considerably, resulting in a less expensive device with ease of fabrication.

36 Claims, 6 Drawing Sheets

IONTOPHORETIC DRUG DELIVERY DEVICE AND METHOD OF MANUFACTURING THE SAME

RELATED APPLICATION

Benefit of the earlier filing date of Provisional Patent Application Ser. No. 60/038,131, filed Mar. 3, 1997, is claimed for this application under Section 119(e) of Title 35 of the United States Code.

BACKGROUND OF THE INVENTION

1. The Field of the Invention

The present invention relates to iontophoretic drug delivery devices, and methods of manufacturing the same.

2. The Relevant Technology

There is an ongoing search for methods of medication delivery which are less invasive, less painful, and more efficient than conventional methods. For example, hypodermic injection of medication commonly entails pain and risk of infection. Oral ingestion of medication entails absorption of the drug from the digestive tract into the blood stream, wherein the blood containing the drug first percolates through the liver before entering the general circulation for delivery to the target tissue. In turn, much of an orally ingested drug may be metabolically inactivated before it has a chance to exert its pharmacologic effect. Local delivery of drugs therefore presents advantages over oral administration, an application characterized by inefficiency and unpredictability, and over hypodermic injection, an invasive, inconvenient, and sometimes risky technique.

One such local delivery method is known as iontophoresis. Iontophoresis is a safe, effective, non-invasive, and relatively painless medication delivery system. Iontophoresis involves the interaction between ionized molecules of a drug and an external electric field, resulting in the migration of charged molecules. The migration is achieved by placing two electrodes on the patient's skin, and connected to a DC power supply. One of the electrodes is an "active" electrode filled with a drug solution. The other electrode is an "inactive" electrode filled with an electrolyte solution. The electric field generated between the two electrodes causes the charged drug molecules to migrate from the active electrode into the tissues and blood stream of the patient.

Iontophoretic devices conventionally include a circuit board, electrodes and drug reservoirs which are fabricated separately, and then incorporated, together with electrical connections, in a housing. Rigid elements have conventionally been preferred over flexible elements because it was believed that it was easier to manipulate and maneuver rigid elements relative to one another in restricted spaces. Further, it was believed that rigid elements would not bend or deform during the assembly process, making the task more suitable for automation. However, rigid elements have proved less than ideal for suitable conformance to the body of a patient.

The device of U.S. Pat. No. 5,314,502 (hereinafter, "the '502 patent) is directed to a device which is flexible enough to conform to the contours of a patient's body. The '502 patent discloses an iontophoretic delivery device comprising a flexible housing having a flexible printed circuit board mounted therein, and a battery connected to the flexible printed circuit board. The flexible printed circuit board is connected to a pair of electrodes which each sit on top of a reservoir Each reservoir is in contact with the skin during in use.

However, certain problems are associated with the device of the '502 patent. The flexible printed circuit board carries a number of integrated circuit elements on its upper surfaces within a cavity in the flexible housing. The flexibility necessary to ensure conformity with the contours of the body means that the integrated circuits can be damaged by pressure exerted on the housing or by a shock occurring which could cause the integrated circuits to be crushed within the housing.

Furthermore, the battery, electrodes and connecting wiring are embedded within the housing making manufacture of the device difficult to achieve, which increases the expense of the device.

SUMMARY AND OBJECTS OF THE INVENTION

It is an object of the present invention to provide an iontophoretic device which conforms to the body of a patient while sufficiently protecting the components of the device.

Another object of the present invention is to provide an iontophoretic device which increases the ease and decreases the cost of manufacture associated with conventional devices.

Still another object of the present invention is to provide methods for manufacturing an improved iontophoretic device.

These and other objects and features of the present invention will become more fully apparent from the following description and appended claims, or may be learned by the practice of the invention as set forth hereinafter.

To achieve the forgoing objects, and in accordance with the invention as embodied and broadly described herein, the present invention relates to new and useful apparatus and methods for improving the comfort and performance of iontophoretic devices and to simplifying the construction of such devices to assist in manufacture and thereby reduce costs.

Specifically, an iontophoretic drug delivery device in accordance with the present invention comprises a flexible reservoir sandwiched between a flexible printed circuit board and a pair of flexible electrodes. A rigid top cover is mounted on a spine on the reservoir by means of snap-fit connections. The rigid cover protects the device from damage while the flexible reservoir, circuit board and electrodes can conform to the skin of a subject. The configuration of the flexible elements allows the manufacturing process to be simplified considerably, resulting in a less expensive device with ease of fabrication.

In an alternate embodiment of the present invention, the circuit board and delivery electrode are combined into a single flexible structure which is provided with means for accommodating the reservoir means between the circuit board and the delivery electrode.

BRIEF DESCRIPTION OF THE DRAWINGS

In order to more fully understand the manner in which the above-recited and other advantages and objects of the invention are obtained, a more particular description of the invention will be rendered by reference to a specific embodiment thereof which is illustrated in the appended drawings. Understanding that these drawings depict only a typical embodiment of the invention and are not therefore to be considered to be limiting of its scope, the invention in its presently understood best mode for making and using the same will be described and explained with additional specificity and detail through the use of the accompanying drawings in which.

DETAILED DESCRIPTION OF THE PREFERRED EMBODIMENTS

Iontophoretic drug delivery involves using an electric current passing through the skin between an active electrode and a counter electrode to deliver an ionic drug from a reservoir through the skin.

Conventionally, iontophoretic devices have been manufactured with substantially rigid elements. While the rigidity promotes ease of manufacture and stability of the device, it prevents the device from adequately conforming to body of a patient.

Alternatively, a flexible housing has been utilized in an attempt to improve the fit of the device on a patient's body. However, this flexible housing does not adequately protect the integrated circuits in the device which can be crushed by pressure exerted on the housing. Further, this approach is expensive and difficult to manufacture because the components such as the integrated circuits, electrodes, and reservoirs are embedded in the housing.

In contrast, the present invention provides an iontophoretic device with improved conformance to the body of a patient without the disadvantages of vulnerability arising from a flexible housing. It is a feature of the present invention that the iontophoretic device comprises a flexible reservoir, electrode and flexible circuit board. A rigid top cover protects the device from damage while the flexible reservoir, circuit board and electrodes enable improved conformance to the skin of a subject. The configuration of the flexible elements allows the manufacturing process to be simplified considerably, which reduces the expense of the device.

The term "iontophoretic" as used herein encompasses iontophoretic, electrophoretic and electro-osmotic delivery (in which a non-ionic drug is assisted in diffusing across the skin transdermally by the application of an electric field, as opposed to being driven in ionic form by the current).

Figure 1:
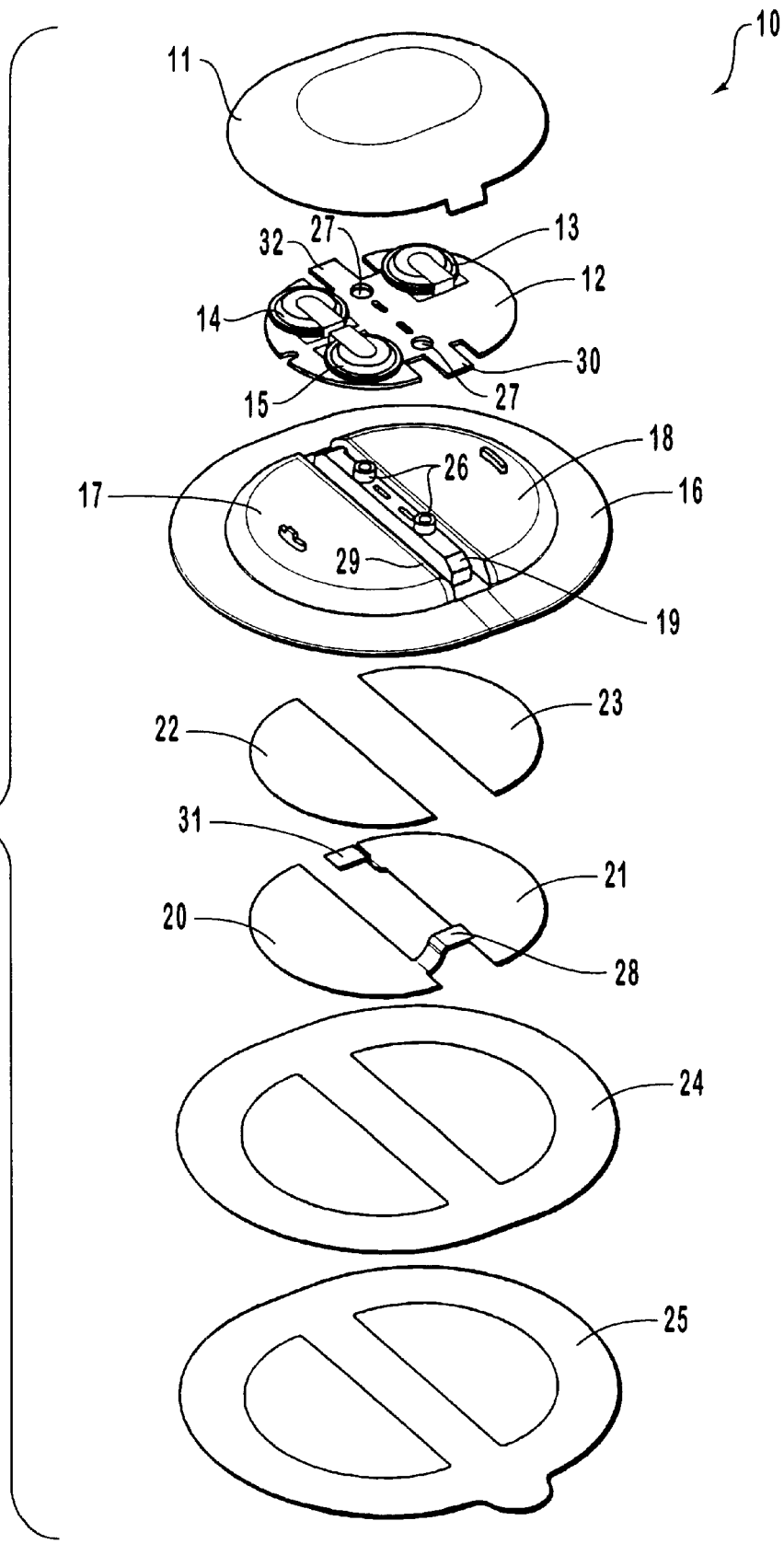
FIG. 1 is an exploded, perspective view of an iontophoretic drug delivery device according to the invention.

Turning to the Figures, in FIG. 1 there is indicated, generally at 10, an iontophoretic 26 drug delivery device according to the invention. The device 10 comprises a rigid protective cover 11, a flexible printed circuit board 12, reservoir means 16, and a pair of electrodes 20,21.

The rigid cover serves to protect the sensitive components of the device as a whole from shock or externally applied pressure. Furthermore, the use of a rigid cover allows a robust device to be produced without necessitating an enclosing housing, and this enables manufacture to be greatly simplified. It has been found that a particularly advantageous construction is to assemble the circuit board, reservoir means and electrodes as a flexible unit before finally adding the rigid cover. Again, because no housing per se is required, the assembly process is speeded up considerably.

The rigid cover 11 preferably comprises an injection molded acrylonitrile-butadiene-styrene polymer (ABS) component. It should be appreciated that other materials that provide suitable protection and ease of manufacture are within the scope of the present invention.

The rigid protective cover is mounted on either the circuit board 12 or on the reservoir means 16 such that the circuit board 12 is positioned between the reservoir means 16 and the rigid protective cover 11.

The rigid cover 11 preferably has a pair of snap-fit stud formations (not shown) on its underside which are received in corresponding snap-fit socket projections 26 located on spine 19 of reservoir means 16. The combination of the snap-fit stud formations and the snap-fit socket projections is one embodiment of a mounting means for mounting the rigid protective cover on the reservoir means 16.

The mounting means comprising socket and stud projections effectively holds the circuit board in position between the reservoir means and the cover. Socket projections 26 pass through apertures 27 on flexible circuit board 12, such that when rigid cover 11 is snap-fitted to reservoir means 16, the mounting means holds the flexible printed circuit board 12 firmly in position. Thus, the circuit board 12 is protected between rigid cover 11 and reservoir means 16.

Preferably, the mounting means comprises complementary formations carried on the rigid cover and on the flexible reservoir means, respectively. Particularly suitable examples of complementary formations include snap-fit components which engage securely with one another when pressed together. Such components allow a device to be assembled without welding or similar steps being required. It should be appreciated that other mounting means are within the scope of the present invention.

The flexible printed circuit board is preferably shaped to accommodate the mounting means. By providing the circuit board with a shape which accommodates the mounting means, further steps to secure the circuit board to the cover or reservoir are unnecessary. For example, where snap-fit formations are provided on the cover and reservoir means, such as in the form of a stud and socket, the circuit board can be provided with an aperture through which the stud or socket passes. When the stud and socket are pressed together the circuit board is automatically retained with the mounting means passing through the aperture on the circuit board. The mounting means can be designed to fit together leaving a gap between the cover and reservoir sufficient to just accommodate the circuit board in position.

A preferred control means in accordance with the present invention comprises an electrical circuit carried on flexible printed circuit board 12. The flexible printed circuit board 12 preferably includes three 3V lithium coin cell batteries 13,14,15 mounted thereon. It should be appreciated that other control means are within the scope of the present invention.

In a preferred embodiment of the present invention, the control means includes means for detecting the application of the device to the skin and means for commencing delivery of drug from the reservoir upon said detection of application to the skin. Preferably, the detecting means comprises a skin contact sensor connected to a power source. The means for commencing delivery preferably comprises a switch forming part of the electrical circuit which is activated upon detection of skin contact by the skin contact sensor.

It is preferred that the control means additionally include means for gradually increasing the current flowing through the electric circuit from an initial value of zero before commencement of delivery to a first value which is higher than the steady state value required, maintaining the first value for a predetermined period of time, and then reducing the current to a steady state value and maintaining the steady state current throughout the duration of delivery.

The provision of a higher initial current is advantageous in that it serves to quickly build up levels of the drug after application of the device. In the case where the drug is an analgesic, for example, the patient may require rapid pain relief, and with many other classes of drug it may also be preferable to achieve therapeutic levels as quickly as possible.

Preferably, the time taken to increase the current from zero to the first, higher value is from 2 minutes to thirty minutes, and more preferably from 5 minutes to fifteen minutes.

Preferably the current is maintained at this value for between ten minutes and three hours, and more preferably for between thirty minutes and two hours.

A further preferred feature is that the first, higher value is between 1.5 times and 10 times the steady state value, more preferably between 1.5 times and 4 times the steady state value.

In a presently preferred embodiment, the first, higher value is 0.75–1.0 mA, the steady state value is 0.25–0.50 mA, the time taken to reach the first, higher value is 8–12 minutes, and the first, higher value is maintained for 45–60 minutes before the current drops to the steady state value.

A further preferred feature of the present invention is that the control means comprises means for controlling the current through a programmed routine, and means for detecting the removal of the device from the skin and for recommencing the programmed routine at the point at which it was interrupted by the removal of the device from the skin. This feature allows a user to remove the device and reposition it if for any reason it is placed in an unsuitable location (e.g. it may be physically uncomfortable or the skin on which it is placed may be unusually sensitive), without interfering with the cycle. It also allows a user to remove a device which has a twenty-four hour delivery cycle, for example, to be removed from the skin during short periods such as when bathing or playing sports, before being returned to the skin to complete the cycle of delivery.

Preferably, the means for detecting removal and recommencing the routine at the point of interruption remains inoperative, in use, for an initial period of up to 10 minutes, 5 minutes or 3 minutes. The reason for waiting for a brief period before starting delivery is that the possibility exists that a current may exist briefly before the device is applied to the skin. If the circuit includes means for detecting the application of the device to the skin and means for commencing delivery of drug from the reservoir upon the detection of application to the skin, then a false indication of current flowing through the circuit will start operation of the device and drain the battery.

For example, when a device is in storage, a strong electromagnetic field such as might occur during a thunderstorm could be interpreted as a current flowing through the skin detection means, especially if the current sensor is particularly sensitive, as is the preferred case. Alternatively, the delivery circuit could be accidentally actuated if the device is removed from packaging and the electrodes are touched briefly before it is intended to apply the device to the skin. By providing the "latch" circuit which requires continuous detection for a period of time of 3, 5 or 10 minutes, these false indications of application to skin are avoided.

Figure 6:
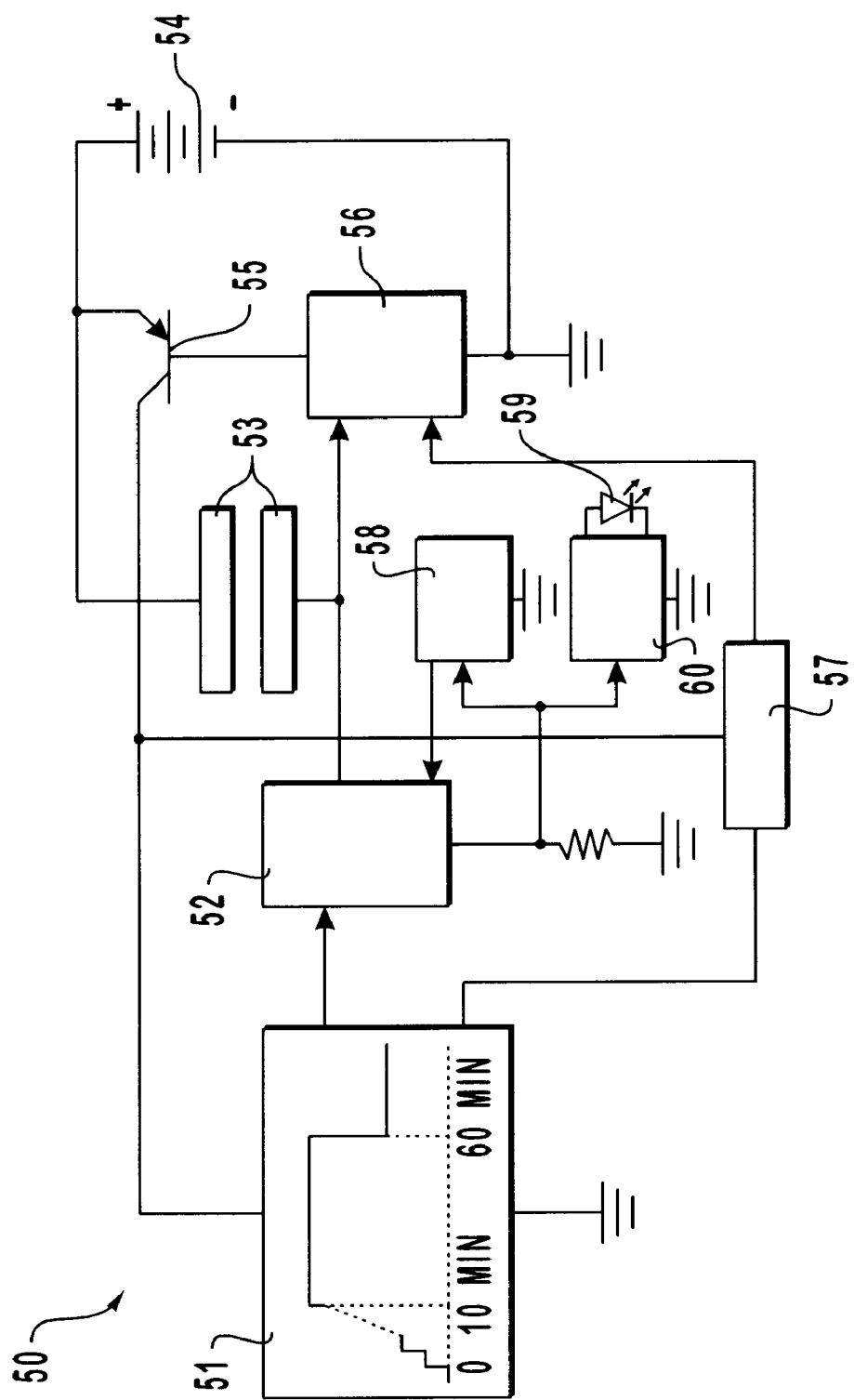
FIG. 6 is a block diagram of the electrical circuit of the devices of FIGS. 1 and 5.

The controlling circuitry of the device is illustrated in block diagram format in FIG. 6. The circuit shown in the form of a block diagram in FIG. 6 is shown in detail in FIG. 7, in which all components and notations have their customary meaning within the art. The layout of the circuit in FIG. 7 follows the same general spatial configuration as the block diagram of FIG. 6.

The circuit, indicated generally at 50 in FIG. 6 comprises a programmer 51 which is provided with instructions for a given current profile. In an embodiment of the present invention such as that described above and with hydromorphone as the active ingredient, a suitable current profile is as follows: the current starts from zero at the beginning of the delivery regime (i.e. t=0), rising in 16 steps of 52 $\mu$A over the first ten minutes (i.e. until t=10 min). The final current is stabilized at a level of 0.83 $\mu$A, and is maintained at this first, higher level from t=10 to t=60 min. The current then drops to a lower, steady state level for the remainder of the delivery period, in this case from t=60 min to t=30 hours. Although the device is designed to be a once-daily device, the extension of delivery to 30 hours rather than 24 hours takes account of the fact that delivery should be maintained even if the patient does not change the device at the same time every day.

The programmer 51 generates voltages which are fed to a current regulator 52 which translates the voltages generated by the programmer 51 into stabilized current levels, so as to supply a steady output independently of the battery voltage (which may fluctuate) and independently of voltage drops between the two electrodes 53. Electrodes 53 serve to deliver the drug when applied to the skin.

Figure 7:
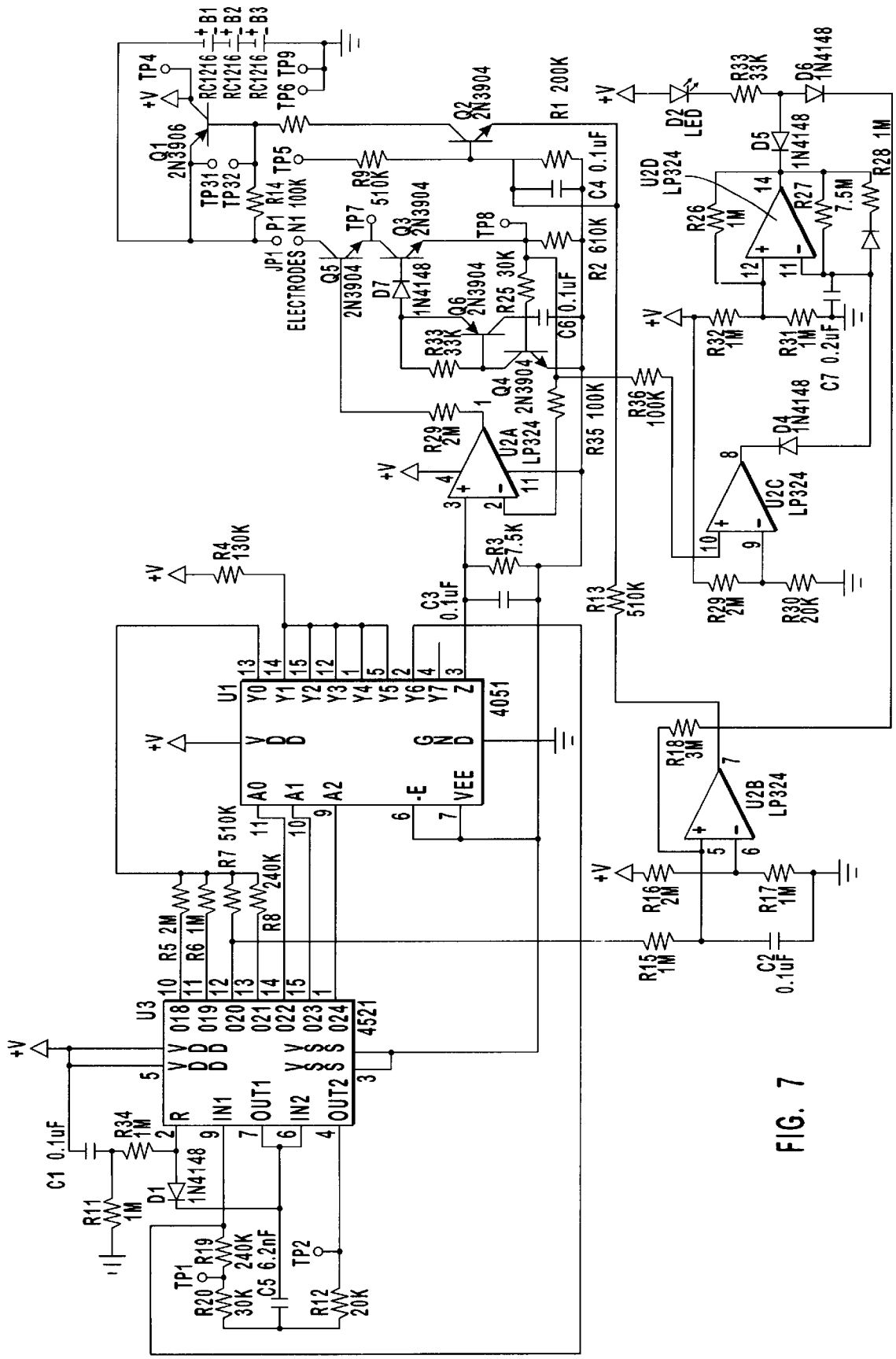
FIG. 7 is the block diagram of FIG. 6 shown in detail.

A battery 54 is connected to programmer 51 and current regulator 52 across a transistor 55 (transistor Q1 in FIG. 7). Transistor 55 is controlled by a skin contact sensor 56 which detects the closing of a circuit across electrodes 53. Before the device is applied to the skin, skin contact sensor 56 detects that the circuit between the electrodes 53 is open, and the power supply from battery 54 to programmer 51 and current regulator 52 is cut off by transistor 55. When skin contact sensor 56 detects the application of the electrodes 53 to the skin, it switches transistor 55 so as to connect battery 54 to programmer 51 and current regulator 52, thereby beginning delivery.

A latch circuit 57 is connected between programmer 51 and skin contact sensor 56. After a given period of time (e.g. 2.5 minutes) programmer 51 sends a signal to latch circuit 57. After this signal is received, if the device is removed from the skin the programmer will resume the delivery upon re-application from the point at which the cycle was interrupted. Thus, once the latch circuit is activated, the device can be removed for repositioning. If the skin contact sensor 56 detects only a short (<2.5 min) current flow, the latch circuit 57 will not be operated and removal of the device from the skin will switch off the circuit, thereby preventing battery drainage occurring as a result of a briefly closed circuit or a strong electromagnetic field.

An over-current protector 58 continuously monitors the current provided by current regulator 52 and cuts off the current through the electrodes 53 if the current rises above a predetermined level (e.g. 1 mA) at which skin burning or excessive dosage levels might begin to occur.

A light emitting diode (LED) 59 is driven by an LED driver 60 which includes an oscillator. The LED 59 provides an indication of the proper ftnctioning of the circuitry. During the first two minutes of delivery, LED 59 is continuously lit, and once the latch circuit 57 is activated, driver 60 causes the LED to flicker continuously throughout delivery.

Returning to FIG. 1, the circuit board 12 is preferably mounted between the rigid cover 11 and the flexible reservoir means 16. Suitably, the flexible reservoir means is provided with a substantially rigid section which engages the formations forming part of the mounting means as described hereinabove. Preferably, the substantially rigid section is disposed along a central line separating two or more flexible sections, each of the flexible sections being a separate reservoir forming part of the flexible reservoir means.

For example, in FIG. 1, a rigid spine 19 is provided between two halves of a reservoir body. The spine provides the strength to hold the reservoir (and thus also the circuit board and delivery electrode) in position relative to the cover, while the remainder of the reservoir body provides the requisite flexibility to conform to the contours of the body.

In a preferred embodiment of the present invention, reservoir means 16 is made by injection molding or vacuum forming an elastomer material sold by Shell Chemicals under the Trademark "KRATON G2705," which is a thermosetting polymer compound with saturated rubber midblock. This elastomeric reservoir cushions circuit board 12 from below, while rigid cover 11 protects circuit board 12 from above.

Preferably, the reservoir means is sandwiched between the circuit board and the delivery electrode. This "sandwich" construction leads to the signal flexible unit referred to above on which the cover can be conveniently mounted in the final stage of assembly.

The flexible reservoir means has opposed first and second surfaces. FIG. 1 illustrates the second surface of the flexible reservoir means which comprises two reservoir wells 17,18 separated by rigid spine 19. Two electrodes 20, 21 are provided on the first surface of the reservoir means.

In the illustrated embodiment, reservoir well 17 contains an active formulation, and reservoir well 18 contains a "counter" (inactive) formulation which is used to ensure a good iontophoretic circuit. One preferred active formulation consists of 0.5% methyl paraben (preservative), glycerol, agar, and the active ingredient which in this case is the analgesic hydromorphone. The counter formulation preferably consists of glycerol, agar, water and sodium chloride.

The two electrodes preferably comprise a flexible substantially flat delivery (active) electrode and a flexible counter (passive) electrode. Each of the electrodes is preferably a porous, flexible conductive member. Preferably, each electrode is in the form of a polymeric film coated with electrically conductive material.

In a preferred embodiment, electrode 20 is a delivery electrode comprising a layer of 0.15 mm polyester film on which a layer of silver ink is printed. A pure silver layer having a thickness of 16 microns is plated onto the ink.

Further, electrode 21 is a counter electrode comprising a layer of 0.15 mm polyester film on which a layer of silver ink is printed. A pure silver layer having a thickness of 8 microns is plated onto the ink and then the film is dipped into a ferric chloride solution to provide a silver/silver chloride outer layer.

A conductive strip 28 on delivery electrode 20 passes through an aperture 29 in reservoir means 16 to contact a terminal 30 of circuit board 12, thereby enabling power to be transmitted from the batteries 13,14,15 to electrode 20 via a control circuit which is printed on circuit board 12. Alternatively, the control circuit can be in the form of an integrated circuit mounted on board 12. A similar conductive strip 31 contacts a terminal 32 on circuit board 12 to complete the return circuit (the circuit is closed when the device is applied to the skin).

The electrodes 20,21 are adhered to reservoir means 16 by two adhesive patches 22,23, respectively. A further layer of adhesive 24 is positioned on the underside of reservoir means 16 around the electrodes 20,21. The adhesive used to attach the electrodes to the reservoir means and to attach the underside of reservoir means to the skin of the patient is preferably an electrically conductive dermal adhesive such as that available under the Trademark MA46 from Adhesives Research, Glen Rock, Pa., U.S.A. The resistance of the adhesive can be chosen by using a different adhesive or by varying the thickness of the adhesive, in order to obtain the desired current through the skin.

A release liner 25 protects electrodes 20,21 and adhesive 24 before use. One preferred release liner in accordance with the present invention is release liner number 7010 sold by Adhesives Research.

The device is assembled by adhering the electrodes 20,21 to reservoir means 16, positioning circuit board 12 on reservoir means 16 (such that socket projections 26 protrude through apertures 27, and terminals 30,32 are in contact with conductive strips 28,31, respectively), and pressing rigid cover 11 downwards to snap the mounting means together. Adhesive layer 24 is applied to the underside of reservoir 16 and finally release liner 25 is applied to the underside of the device 10.

Figure 2:
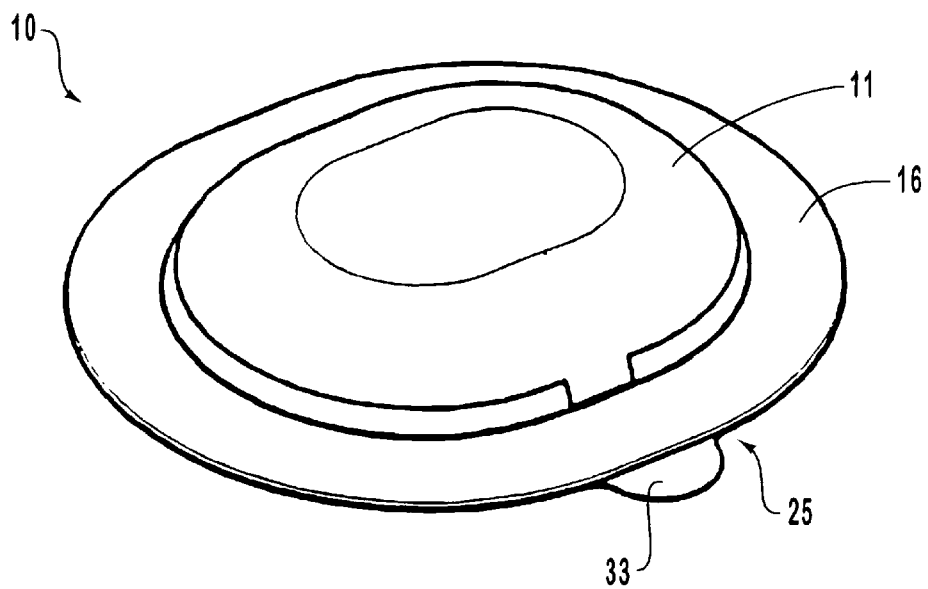
FIG. 2 is a perspective view of the device of FIG. 1.
Figure 3:
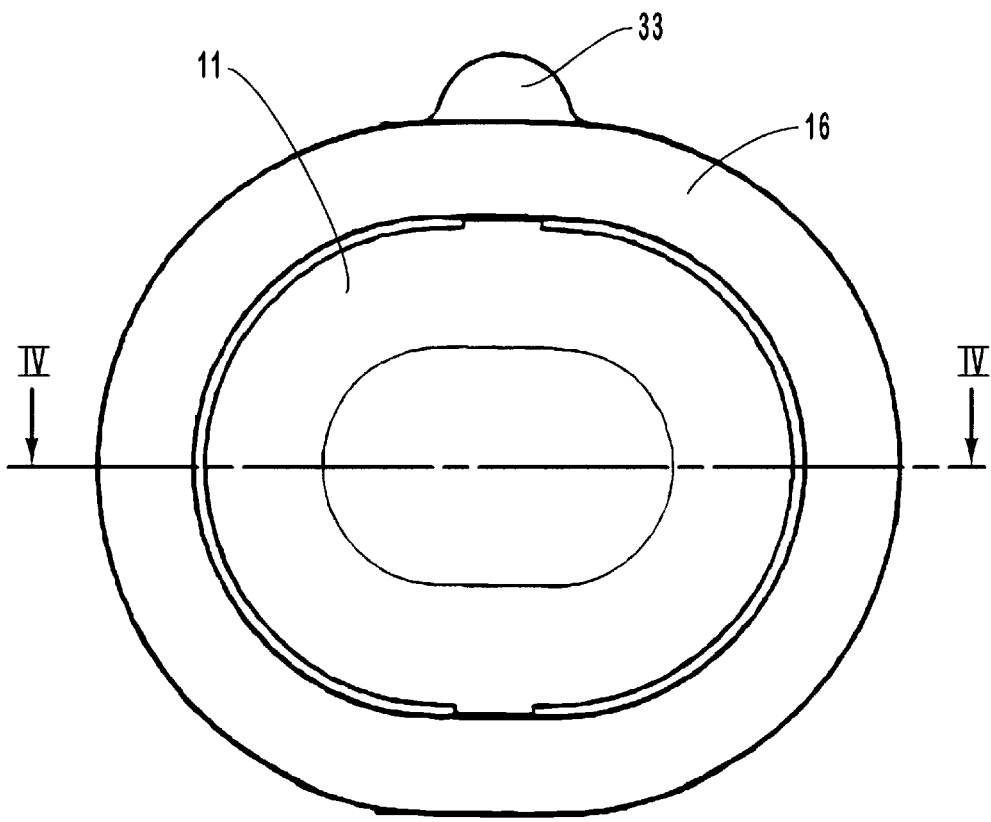
FIG. 3 is a plan view of the device of FIG. 1.

The assembled device is illustrated in perspective view in FIG. 2 and in plan view in FIG. 3. In each of FIGS. 2 and 3, rigid cover 11, the periphery of reservoir means 16 and a tab 33 of release liner 25 can be seen.

Figure 4:
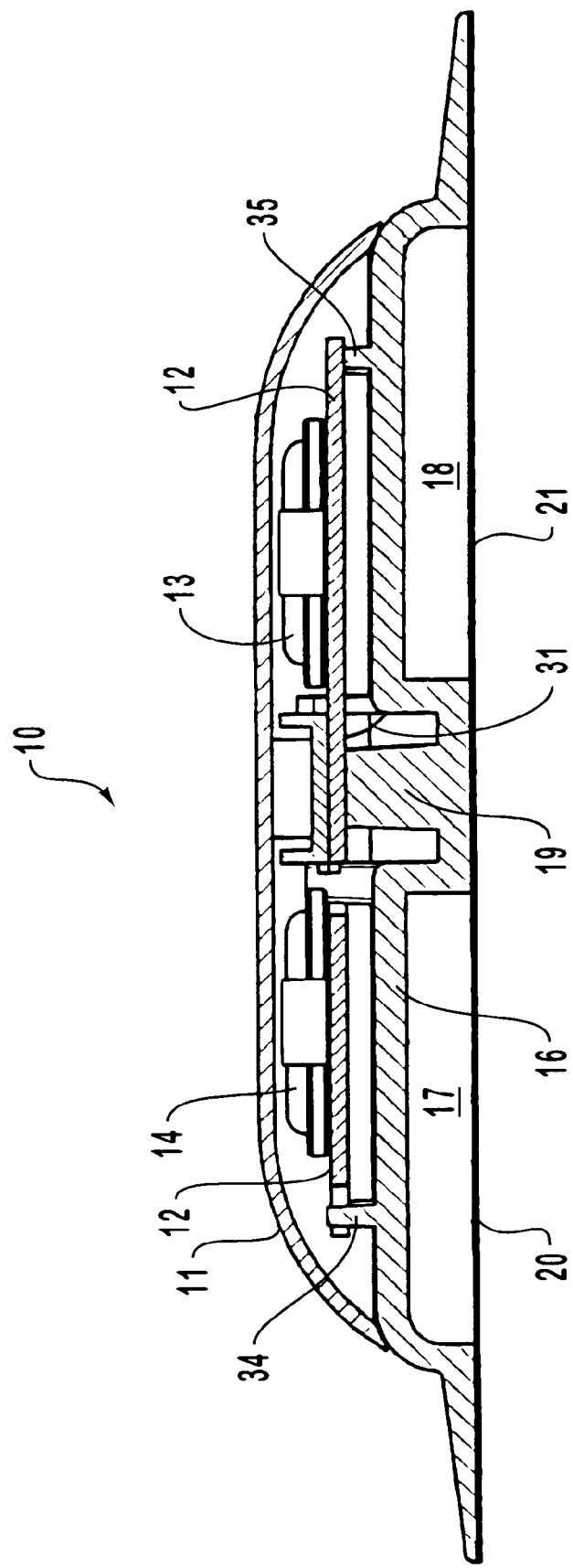
FIG. 4 is a sectional view of the device of FIG. 1.

FIG. 4 depicts a sectional view of device 10, taken along the line IV—IV from FIG. 3. It will be appreciated from FIG. 4 that cover 11 and reservoir means 16 essentially "sandwich" flexible circuit board 12 therebetween.

Circuit board 12 rests on spine 19 and projections 34,35 which are formed on the upper surfaces as wells 17,18 respectively. Batteries 13,14 can be seen mounted on circuit board 12, and conductive strip 31 can be seen extending up to contact circuit board 12. The electrodes 20,21 on the underside of the device 10 can also be seen.

In addition, it can be appreciated from FIG. 4 that rigid cover 11 is connected to the remainder of the device only along the central spine 19, thereby allowing the device to flex and conform to the contours of the body to which it is applied, while still protecting the flexible circuit board from pressure or impact. Importantly, this is achieved by a construction which an be snap-fitted together which does not require a housing to contain all of the elements.

Alternatively, in a particularly preferred embodiment of the present invention, the circuit board and the delivery electrode form part of a single flexible structure which is provided with means for accommodating the flexible reservoir means between the circuit board and the delivery electrode. It has been found that the use of a single flexible body is particularly advantageous because it allows the "electrical" (or electrochemical) elements of the device to be manufactured together as part of a single process, prior to assembling this flexible component in place with the reservoir means. Suitably, the single flexible structure comprises a flexible member which serves as both the flexible circuit board and the flexible delivery electrode.

For example, a polymeric film can be used as an inert substrate. Part of the substrate can be converted into a flexible circuit board by conventional means (such as printing electronic circuitry using conductive inks) and part can be converted into an electrode by depositing a conductive layer (such as a silver layer which forms a particularly effective electrode in combination with a silver chloride counter-electrode). The combined flexible circuit board/ flexible electrode is then assembled in place on the flexible reservoir.

Figure 5:
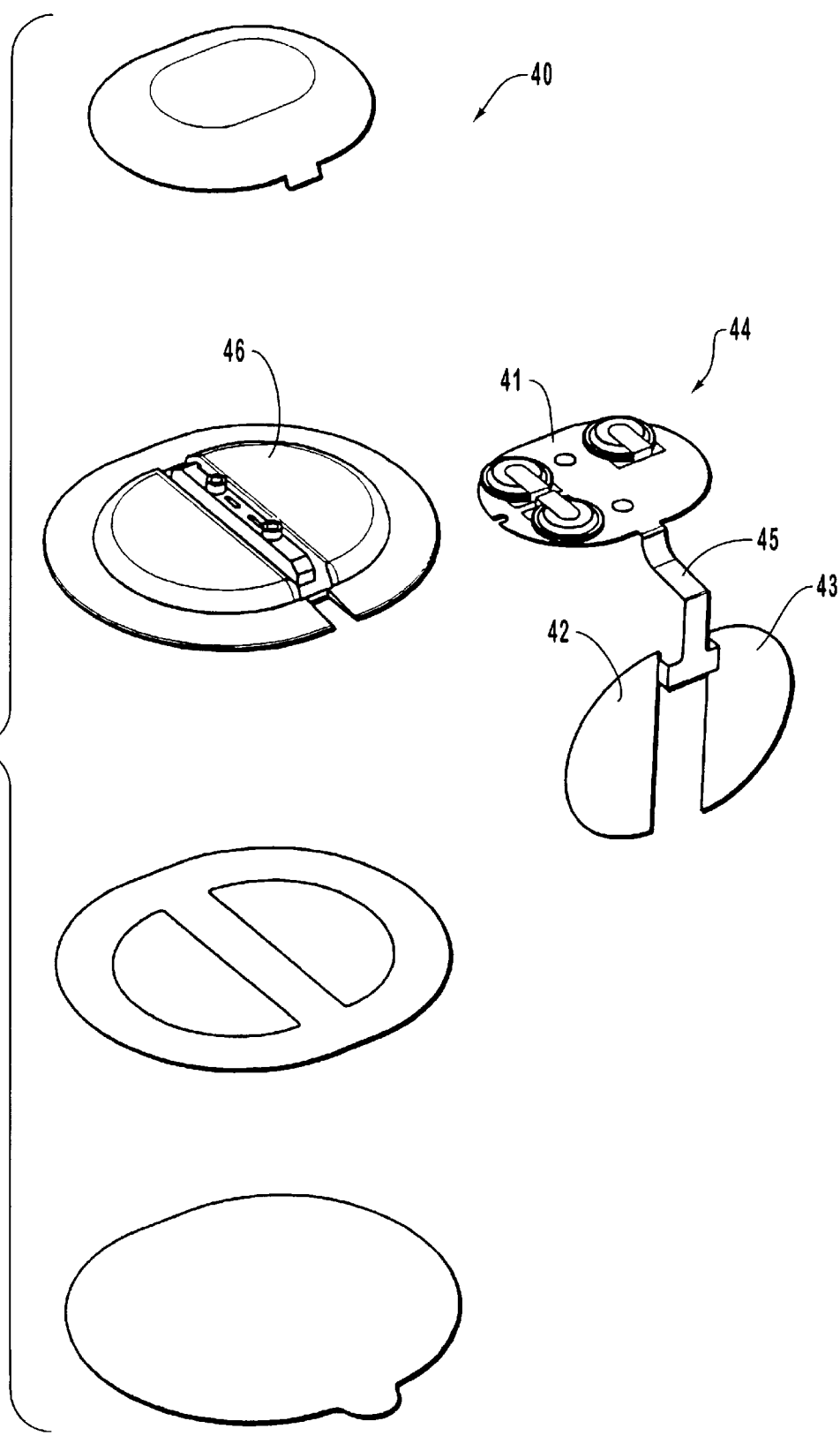
FIG. 5 is an exploded view of an alternative embodiment of a drug delivery device according to the invention.

This alternate embodiment of the present invention is illustrated generally at 40 in FIG. 5. Although the FIG. 5 embodiment is identical to that of FIGS. 1–4 in many respects, the FIG. 5 embodiment employs a flexible circuit board 41 and electrodes 42,43 which form part of a single flexible structure, indicated generally at 44. A flexible connecting strip 45 between the circuit board 41 and electrodes 42,43 enables the structure 44 to be affixed to reservoir means 46 by sandwich reservoir means 46 between circuit board 41 and electrodes 42,43.

This construction provides advantages in terms of ease of manufacturing, since it is not necessary to effect a connection between the circuit board 41 on one side of the reservoir means 46 and the electrodes 42,43 on the other side thereof (since the connection already exists as connecting strip 45, on which connecting circuitry is printed in conductive ink. Preferably, a single substrate forms the basis for structure 44, with circuit board 41 comprising a portion of the substrate on which controlling circuitry has been printed, and electrodes 42,43 comprising portions which have been treated (as described above in relation to FIGS. 1–4) to become electrodes.

Alternatively, structure 44 is assembled initially from a flexible circuit board, flexible connecting strip and flexible electrodes which are bonded together to provide a single structure containing all of the electrical/electrochemical elements of the device, this structure then being assembled into place relative to the reservoir means.

In another aspect of the invention, there is provided a method of manufacturing an iontophoretic drug delivery device. The method of manufacture is, as explained above, significantly faster and less complicated than assembling a plurality of flexible elements in the interior of a flexible housing, as well as providing a product which combines the advantage of flexibility and rigidity referred to above.

Even a small increase in the speed or ease of assembly provides a significant commercial advantage. Further, eliminating the need for any housing provides a significant decrease in the complexity of the manufacturing operation.

The speed, ease and lack of complexity of the assembly process enable the device to be made quicker, cheaper and with a better overall quality. Moreover the improved assembly process will decrease the likelihood of any contamination or desterilization that may occur in the medicament reservoir.

A preferred method in accordance with the present invention comprises the following steps:

A flexible circuit board is interposed between a rigid cover and a flexible reservoir means. The rigid cover and the flexible reservoir means are preferably provided with complementary formations for attachment together, and the flexible circuit board is preferably provided with means for accommodating the complimentary formations;

The complimentary formations are joined together such that the means for accommodating the complimentary formations holds the circuit board in place between the rigid cover and the reservoir means.

A flexible substantially flat delivery electrode is placed on the surface of the reservoir means distal from the circuit board.

Preferably, the delivery electrode is adhered to the reservoir by means of an electrically conductive adhesive.

It should be noted that these steps are not necessarily carried out in the order in which they were presented. For example, it may be preferable to assemble the flexible components together before attaching the rigid cover.

Preferably, the method includes the additional step of covering the exposed surface of the reservoir means and/or delivery electrode distal from the circuit board with adhesive means for adhering the device to the skin of a subject, in use.

The method according to the invention further comprise the step of covering the adhesive means with a release liner which is adapted to be peeled away before use of the device, so as to expose the delivery electrode and the adhesive means for application thereof to the skin of a subject.

In addition, the method according to the invention comprises the step of filling the reservoir means with a drug to be delivered. The reservoir means comprises a plurality of reservoirs and the filling step involves filling different reservoirs with different drugs.

The term "drug" as used herein includes but is not limited to conventional medicaments as well as cosmetic substances or other substances which may be advantageously applied to the skin of a subject. As far as medicaments are concerned, there is essentially no limitation on the type of drug which can be used with the invention other than to exclude those drugs which would be inappropriate to deliver to a subject iontophoretically, electrophoretically or electro-osmotically. Representative drugs include peptides or proteins, hormones, analgesics, anti-migraine agents, anti-coagulant agents, anti-emetic agents, cardiovascular agents, anti-hypertensive agents, narcotic antagonists, chelating agents, anti-anginal agents, chemotherapy agents, sedatives, anti-neoplastics, prostaglandins and antidiuretic agents. Other drugs include anti-ulcer agents, antibiotics, anticonvulsants, antiinflammatories, antifungals, antipsychotics, corticosteroids, immunosuppressants, electrolytes, nutritional agents and vitamins, general anesthetics, antianxiety agents, and diagnostic agents.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An iontophoretic drug delivery device, comprising:
   (a) a flexible reservoir having opposed first and second surfaces and comprising at least one reservoir well adapted to contain a drug to be delivered to a subject in need thereof;
   (b) a flexible, substantially flat, delivery electrode disposed on the first surface of the flexible reservoir;
   (c) a flexible circuit board disposed on the second surface of the flexible reservoir and comprising means for controlling iontophoretic delivery of the drug; and
   (d) a rigid protective cover positioned such that the flexible circuit board is between the flexible reservoir and the rigid protective cover, the rigid protective cover extending laterally sufficiently to cover and thereby protect the flexible circuit board and the at least one reservoir well.

2. The device according to claim 1, wherein the rigid protective cover is attached to the second surface of the flexible reservoir by mounting means, the flexible circuit board being shaped to accommodate the mounting means.

3. The device according to claim 2, wherein the mounting means comprises complementary formations on the rigid protective cover and on the flexible reservoir.

4. The device according to claim 3, wherein the flexible reservoir is provided with a substantially rigid section which carries the complementary formations on the flexible reservoir.

5. The device according to claim 4, wherein the substantially rigid section is disposed along a line separating two or more flexible sections of the flexible reservoir, each of the flexible sections comprising a separate reservoir well of the flexible reservoir.

6. The device according to claim 1, wherein the flexible circuit board and the flexible delivery electrode form part of a single flexible structure shaped to accommodate the flexible reservoir between the flexible circuit board and the flexible delivery electrode.

7. The device according to claim 1, further comprising a flexible counter-electrode disposed on the first surface of the flexible reservoir adjacent to the flexible delivery electrode.

8. The device according to claim 7, wherein each electrode is in the form of a polymeric film coated with electrically-conductive material.

9. The device according to claim 1, wherein the means for controlling iontophoretic delivery of the drug comprises means for detecting application of the device to the skin of the subject and means for commencing delivery of the drug from the at least one reservoir well upon or at a predetermined time period after said detection of application to the skin.

10. The device according to claim 9, wherein the means for detecting application of the device to the skin comprises a skin contact sensor in electrical communication with a power source, and wherein the means for commencing delivery of the drug comprises a switch which is activated upon or at a predetermined time period after detection of skin contact by the skin contact sensor.

11. The device according to claim 1, wherein the means for controlling iontophoretic delivery of the drug comprises means for increasing a current from an initial value of zero before commencement of delivery of the drug to a first value which is higher than a steady-state value, maintaining the current at the first value for a predetermined amount of time, decreasing the current to the steady-state value, and maintaining the current at the steady-state value.

12. The device according to claim 11, wherein the time taken to increase the current from zero to the first value is from 2 minutes to 30 minutes, and the current is maintained at the first value for between 10 minutes and 3 hours.

13. The device according to claim 12, wherein the time taken to increase the current from zero to the first value is from 5 minutes to 15 minutes, and the current is maintained at the first value for between 30 minutes and 2 hours.

14. The device according to claim 11, wherein the first value is between 1.5 times and 10 times the steady-state value.

15. The device according to claim 14, wherein the first value is between 1.5 times and 4 times the steady-state value.

16. The device according to claim 11, wherein the first value is 0.75 to 1.0 mA, the steady-state value is 0.25 to 0.50 mA, the time taken to increase the current from zero to the first value is 8 to 12 minutes, and the current is maintained at the first value for 45 to 60 minutes before being decreased to the steady-state value.

17. The device according to claim 1, wherein the means for controlling iontophoretic delivery of the drug comprises means for controlling a current through a programmed routine, means for detecting application and removal of the device from the skin of the subject, and means for interrupting programmed routine upon detection of removal of the defice from the skin of the subject and for recommencing the programmed routine at the point of interruption upon detection of application of the device to the skin.

18. The defice according to claim 17, wherein the means for interrupting and recommencing the programmed routine is inoperative for an initial period of up to 10 minutes after detection of application to the skin.

19. The device according to claim 18, wherein the initial period is 5 minutes or less.

20. The device according to claim 19, wherein the initial period is 3 minutes or less.

21. A method of manufacturing an iontophoretic drug delivery device, comprising the steps of:
   (a) interposing a flexible circuit board between a rigid protective cover and a flexible reservoir having at least one reservoir well, the rigid protective cover and the flexible reservoir being provided with complementary formations for attachment together and said flexible circuit board being shaped to allow said complementary formations to attach together;
   (b) joining the complementary formations together such that the flexible circuit board is held in place between the rigid protective cover and the flexible reservoir, and the rigid protective cover extends laterally sufficiently to cover and thereby protect the flexible circuit board and the at least one reservoir well; and
   (c) providing a flexible, substantially flat delivery electrode on a surface of the flexible reservoir distal from the flexible circuit board.

22. The method according to claim 21, wherein step (c) comprises adhering the flexible delivery electrode to the flexible reservoir with an electrically conductive adhesive.

23. The method according to claim 21, wherein the flexible circuit board and the flexible delivery electrode are provided as a single flexible structure shaped to accommodate the flexible reservoir between the flexible circuit board and the flexible delivery electrode.

24. The method according to claim 21, further comprising the step of covering an exposed surface of the flexible reservoir distal from the circuit board, an exposed surface of the delivery electrode distal from the circuit board, or both, with an adhesive layer.

25. The method according to claim 24, further comprising the step of covering said adhesive layer with a release liner which is adapted to be peeled away before use of the device, so as to expose said delivery electrode and said adhesive layer.

26. The method according to claim 21, further comprising the step of filling the reservoir well with a drug to be delivered.

27. The method according to claim 26, wherein the flexible reservoir comprises a plurality of reservoir wells and the filling step involves filling different reservoir wells with different drugs.

28. An iontophoretic drug delivery device comprising:
   (a) flexible reservoir means having opposed first and second surfaces;
   (b) a flexible substantially flat delivery electrode carried on the first surface of the flexible reservoir means;

(c) control means comprising an electrical circuit carried on a flexible circuit board mounted on the flexible reservoir means adjacent the second surface thereof; and (d) a rigid protective cover mounted such that the circuit board is positioned between the reservoir means and the protective cover the rigid protective cover being mounted on the reservoir means by mounting means, said mounting means being effective to hold the circuit board in position between the reservoir means and the cover and comprising complementary formations carried on the rioid cover and on the flexible reservoir means, respectively. said circuit board being shaped to accommodate the mounting means, wherein the flexible reservoir means is provided with a substantially rigid section which engages the formations forming part of the mounting means and wherein the substantially rigid section is disposed along a central line separating two or more flexible sections, each of the flexible sections being a separate reservoir forming part of the flexible reservoir means.

29. The device according to claim 28, wherein the flexible circuit board and the flexible delivery electrode form part of a single flexible structure shaped to accommodate the flexible reservoir means between the flexible circuit board and the flexible delivery electrode.

30. The device according to claim 28, further comprising a flexible counter-electrode disposed on the first surface of the flexible reservoir means adjacent to the flexible delivery electrode.

31. The device according to claim 28, wherein each electrode is in the form of a polymeric film coated with electrically-conductive material.

32. The device according to claim 28, wherein the control means comprises means for detecting application of the device to the skin of a subject and means for commencing delivery of a drug from the reservoir means well upon detection of application of the device to the skin.

33. The device according to claim 32, wherein the means for detecting application of the device to the skin comprises a skin contact sensor connected to a power source, and wherein the means for commencing delivery of the drug comprises a switch which is activated upon detection of skin contact by the skin contact sensor.

34. The device according to claim 28, wherein the control means comprises means for increasing a current from an initial value of zero before commencement of delivery of a drug to a first value which is higher than a steady-state value, maintaining the current at the first value for a predetermined amount of time, decreasing the current to the steady-state value, and maintaining the current at the steady-state value.

35. The device according to claim 28, wherein the control means comprises means for controlling a current through a programmed routine, means for detecting application and removal of the device from the skin of a subject, and means for interrupting the programmed routine upon detection of removal of the device from the skin of the subject and for recommencing the programmed routine at the point of interruption upon detection of application of the device to the skin.

36. The device according to claim 35, wherein the means for interrupting and recommencing the program routine is inoperative for an initial period of up to 10 minutes after detection of application the skin.

* * * * *

UNITED STATES PATENT AND TRADEMARK OFFICE
CERTIFICATE OF CORRECTION

PATENT NO. : 5,991,655
DATED : November 23, 1999
INVENTOR(S) : Gross et al.

It is certified that error appears in the above-identified patent and that said Letters Patent is hereby corrected as shown below:

| | |
|---|---|
| Col. 3, line 51 | After the word "iontophoretic" delete -- 26 --. |
| Col. 7, line 27 | Delete "signal" and insert instead -- single --. |
| Col. 9, line 15 | Delete "sandwich" and insert instead -- sandwiching --. |
| Col. 9, line 22 | After the word "ink" insert -- ) --. |
| Col. 12, line 8 | After the word "rupting" insert -- the --. |

Signed and Sealed this

Seventh Day of November, 2000

Attest:

Q. TODD DICKINSON

*Attesting Officer*   *Director of Patents and Trademarks*